(12) United States Patent
Locker et al.

(10) Patent No.: US 6,298,729 B1
(45) Date of Patent: Oct. 9, 2001

(54) CATALYTIC CONVERTER TESTING

(75) Inventors: Robert J. Locker, Corning; Constance B. Sawyer, Lindley, both of NY (US); Douglas J. Fox; James F. Unruh, both of San Antonio, TX (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 09/352,385

(22) Filed: Jul. 13, 1999

(51) Int. Cl.[7] .................................................. G01N 29/00
(52) U.S. Cl. .................................................. 73/668
(58) Field of Search .............................. 73/662, 663, 664, 73/665, 666, 667, 668, 856.6, 856.9, 866, 1.82, 432.1

(56) References Cited

U.S. PATENT DOCUMENTS

| | | |
|---|---|---|
| 4,445,381 | 5/1984 | Russenberger .......................... 73/666 |
| 4,539,845 | 9/1985 | Molimar ................................. 73/668 |
| 5,083,463 | 1/1992 | Marshall et al. ........................ 73/663 |
| 5,597,503 * | 1/1997 | Anderson et al. ..................... 219/552 |
| 5,610,344 * | 3/1997 | Ueda et al. ............................. 73/663 |
| 5,641,910 | 6/1997 | Middleton .............................. 73/668 |
| 5,866,079 * | 2/1999 | Machida et al. ..................... 422/179 |
| 5,895,858 * | 4/1999 | Malone et al. ......................... 73/663 |
| 6,035,715 * | 3/2000 | Porter ..................................... 73/663 |

\* cited by examiner

Primary Examiner—Helen Kwok

(57) ABSTRACT

A method and apparatus for testing the durability of a catalytic converter incorporating a catalyst support honeycomb supported by a resilient mounting material within an exterior converter enclosure, the method comprising vibrating the exterior of the converter enclosure while the converter is heated to a predetermined testing temperature and while the force or acceleration applied to the catalyst support honeycomb by the vibrating exterior enclosure and resilient mounting layer is measured.

20 Claims, 2 Drawing Sheets

CATALYTIC CONVERTER TESTING

BACKGROUND OF THE INVENTION

The present invention relates to a testing method and apparatus for evaluating the mechanical durability of a catalytic converter assembly designed for mounting within the exhaust system of a motor vehicle.

Catalytic converter assemblies must provide a very high level of mechanical and thermal durability because of the harsh conditions of vibration and high temperature encountered in the automotive exhaust system environment. The assembly for a typical catalytic converter includes a catalyst support honeycomb mounted within a protective exterior enclosure, the honeycomb most often being composed of a refractory, high surface area ceramic material for effective support of an active catalyst. To protect the honeycomb from mechanical shock or vibration damage, it is typically supported within the enclosure by a layer of a refractory, resilient mounting material, this layer being pre-compressed in the course of converter assembly to apply a predetermined holding force to the exterior of the honeycomb. In general, it is the deterioration of this resilient layer through exhaust system vibration at high temperature that is the usual cause of honeycomb breakage and ultimate converter failure.

Many different vibration testing systems have been developed to test the resistance of mechanical and electrical components to physical damage under laboratory conditions. Typically, these systems employ vibration tables, activated by electrical or electromechanical means, on which the devices to be tested are mounted for exposure to controlled vibration. U.S. Pat. Nos. 5,083,463 and 5,641,910 are representative of the different table designs which have been developed for such systems.

The use of sensors to collect information about test conditions during vibration testing is also known. U.S. Pat. No. 4,539,845 to Molimar, for example, describes a device for fatigue-testing a mechanical component mounted between armatures activated by an electromagnetic vibrator wherein a displacement sensor is placed between the armatures to generate a sinusoidal feedback signal for controlling vibration conditions.

The design of vibration testing apparatus is of course dictated largely by the conditions to be encountered by the tested part in use. U.S. Pat. No. 4,445,381 to Russenberger, for example, describes a vibration testing apparatus for fatigue testing a part at low frequencies, mainly to avoid part heating that would affect fatigue performance. An important feature of the vibrator design of this apparatus is an arrangement of vibrator isolation springs, and elastomer rods within the vibrator electromagnetic oscillator, that make the resonance frequency of the vibrator independent of the elastic properties of the part under test. The development of higher frequency vibration modes in the system is also suppressed.

A test technique often used to assess the mechanical durability of catalytic converters is the hot vibration test. The hot vibration test is performed using a variety of methods. Most automobile companies have developed their own hot vibration test to simulate accelerated exposure. The test results are judged using a simple pass/fail criterion. Lacking quantitative data there is no possible method for establishing incremental design improvements or defining marginal system durability. That is, if a part fails there is no means of understanding how close it came to failing, or if it fails how close it came to passing.

The hot vibration test most often utilizes an engine as a source for hot gas, and an electrodynamic shaker table for simulating the vehicle vibration. The engines provide a highly variable source of input temperature. The lack of temperature control complicates assessment of the thermal gradient within the converter and consequently the system durability.

The hot vibration test is additionally commonly conducted using a single (e.g. 100 Hz) frequency sine wave vibration exposure. This is unrealistic because most automobiles produce a range of frequencies ranging from a few tens of hertz up to approximately 1000 Hz. In the case of motorcycle engines, vibration frequencies may range from 100 Hz to as high as 2000 Hz, and the need for converter mounting systems capable of withstanding even higher operating temperatures has been recognized. Despite these issues, however, the hot vibration test remains an industry standard for assessing converter durability regardless of its limitations.

SUMMARY OF THE INVENTION

In accordance with the invention, a new testing apparatus and method have been developed to quantitatively evaluate the mechanical durability of catalytic converters under conditions closely approximating those of ordinary or severe anticipated use. The new method and apparatus provide significantly more information about converter mounting systems and mount durability than can be derived from the highly variable, expensive, and qualitative hot vibration tests of the prior art. This is because the mechanical durability of the converter is measured under controlled thermal and vibrational conditions simulating those found in actual engine exhaust systems.

Thermal conditions like those found in typical engine exhaust systems are simulated using heating means that generate heat directly within the interior of the catalyst support honeycomb of the converter, in the same way that heat is generated by catalytic reactions occurring in use. By this means the extent of heating may be controlled to match that specific to a particular vehicle exhaust system being designed. The mechanical forces encountered by the converter assembly in actual use are simulated through the use of an electrodynamic shaker table or other controllable vibration device. Such devices can be programmed to subject the converter to any selected frequency or frequency spectrum that, again, may be appropriate for the design of an exhaust system for a particular vehicle or vehicle type. The vibration table may also be programmed to apply increased levels of input energy to further accelerate the component aging.

In a first aspect, then, the invention includes improved apparatus for the vibration testing of a catalytic converter for a motor vehicle (e.g., a car, truck, bus, motorbike, etc.). Central to the apparatus is a support structure for rigidly supporting the catalytic converter to be tested, and a vibrator connected to the support structure for vibrating the structure and attached converter in a controlled fashion. In most cases, the converter will contain both a ceramic honeycomb catalyst support and a refractory resilient mounting layer supporting the honeycomb within the protective exterior converter enclosure. A preferred support structure for the testing apparatus consists of a load frame, designed for minimal flexure under vibration and incorporating means for attaching to and rigidly supporting the converter enclosure. The vibrator may consist of an electrodynamic vibration table to which the load frame is rigidly attached.

The apparatus further includes a heater for preferentially heating the honeycomb catalyst support mounted within the protective converter enclosure, and a sensor for measuring the force and/or the acceleration experienced by the honeycomb in the course of the vibration test. A suitable heater is an electrical heating element disposed within or adjacent to the honeycomb, while a convenient system for measuring the force being applied to the vibrating honeycomb includes a load cell in direct or indirect contact with the honeycomb during the test.

Certain specialized exhaust system designs, particularly including designs for motorbike exhaust systems, require a converter placement that is either within or directly adjacent to a heated section of the exhaust system, e.g., within an exhaust resonance chamber built into the exhaust line. Successfully simulating the converter environment in such cases requires additionally heating the exterior of the protective converter enclosure during the test. For this purpose the testing apparatus of the invention may include an optional additional external heater designed to apply supplemental heat directly to the exterior of the converter.

Apparatus such as above described facilitates the practice of an improved method for evaluating the durability of a catalytic converter assembly. In accordance with that method, a catalytic converter comprising a ceramic honeycomb supported within a protective exterior converter enclosure by a refractory resilient mounting layer is simultaneously vibrated at one or a plurality of controlled vibration frequencies and at one or more controlled vibration amplitudes while the honeycomb within the enclosure is heated to at least one controlled elevated temperature. At the same time, at least one of the acceleration experienced by, or the force applied to, the supported honeycomb by the combination of the vibrating enclosure and resilient mounting layer is detected and recorded. Preferably, vibration of the converter is accomplished by rigidly attaching the converter to a support which may be activated to vibrate at a predetermined vibration frequency and amplitude, while the detection of honeycomb acceleration or accelerating force is determined by rigidly attaching force or acceleration sensing means to the honeycomb.

BRIEF DESCRIPTION OF THE DRAWINGS

The invention may be further understood by reference to the drawings, wherein.

DETAILED DESCRIPTION

Figure 1:
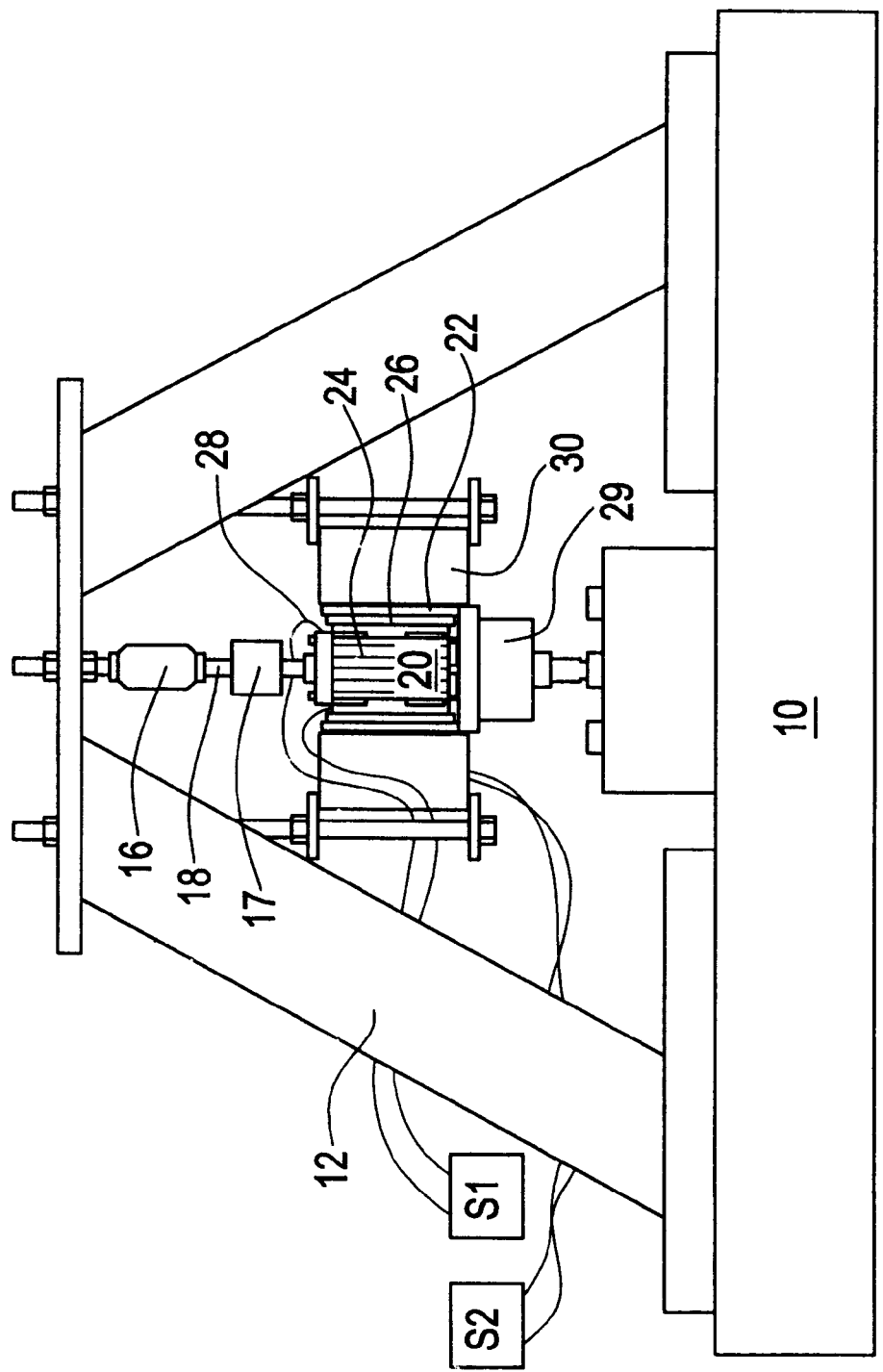
FIG. 1 schematically illustrates converter testing apparatus in accordance with the invention, and FIG. 2 sets forth test data obtained in accordance with the method of the invention.

FIG. 1 of the drawing sets forth an elevational schematic view in partial cross-section view of a preferred embodiment of apparatus for the testing of a catalytic converter in accordance with the invention. The main components of the apparatus include an electrodynamic shaker table 10 supporting a connected load frame 12 to which a catalytic converter 20 is fixedly attached. The catalytic converter includes a protective converter enclosure 22 within which a ceramic catalyst support honeycomb 24 is supported by a layer of refractory resilient supporting material 26. Arranged within the cell structure of catalyst support 24 is an RTE heating element 28 which provides a controlled means for heating the honeycomb to an elevated temperature within a selected range when powered from electricity supplied by power source S1. A heat sink in base support 29 for enclosure 22 can also control converter temperature.

Also mounted on load frame 12 is a load cell 16 for detecting forces applied to honeycomb 24 by the vibrating converter enclosure 22 and resilient support 26. Load cell 16 detects the forces on the honeycomb 24 by means of threaded attachment rod 18 fixedly attached to the honeycomb through thermal isolator 17.

In the operation of this apparatus, vibration table 10 imposes energies of a prescribed frequency and amplitude through base support 29 to converter enclosure 22, those energies then being transmitted across resilient support layer 26 to honeycomb 24. The amplitudes of the excitation energy are chosen to encompass the range of motion that the catalytic converter would encounter on an actual vehicle. The forces transferred across support layer 26 are detected at load cell 16 and recorded.

Optional auxiliary external heater 30 powered by electrical power source S2 is configured to surround enclosure 22. If activated, this external heater can apply external heat to converter enclosure 20 to simulate converter operating conditions found, for example, in motorbike converters.

The force data from the load cell is collected and analyzed as testing progresses. In general, the forces transmitted to the honeycomb during each test will decrease over time in approximate proportion to the number of vibration cycles to which the converter is exposed. This force reduction is attributed to the progressive deterioration of the resilient support layer under the testing conditions imposed. Thus force transferred through the mat to the ceramic is used as a measure of the mat deterioration and consequently a measure of converter mounting system durability.

Typically the vibration test is stopped following a 50% decrease in the peak force carried by the mat, the time to reach this level of mat deterioration being a good measure of mount stability. In fact, in terms of absolute converter performance, taking the 50% decrease point as an arbitrary "failure" point, even though part failure has normally not yet occurred, provides a design limit with a more than adequate margin of acceptable converter performance.

The described testing approach permits excellent flexibility as to the parameters of the tests. The input amplitudes of the applied vibration may be increased to accelerate test severity, and the frequency distribution of the vibration may be set to match exhaust system vibration conditions for particular motor vehicle or vehicle operating condition. Further, the thermal profile developed in the ceramic honeycomb may be precisely controlled, since the RTE wire heating element may be configured to provide either uniform or asymmetric temperature profiles across the honeycomb.

This testing flexibility has aided in defining a key service life parameter applicable to catalytic converter mounting systems, referred to as the "endurance limit". For any candidate mounting system and converter operating temperature, this limit corresponds to the converter vibration amplitude below which no significant mat deterioration is observed even after prolonged exposure to the vibration. If the endurance limit for a converter mounting system is not reached in the environment of intended use, then theoretically the mounting system and honeycomb will never experience a mechanical failure in that environment.

The following Example illustrates the specific application of the invention to the evaluation of comparative catalytic converters for a particular field of use.

EXAMPLE

Comparative testing is undertaken to evaluate two different resilient support materials as candidates for possible use in the manufacture of motorbike catalytic converters. This converter application is particularly severe due to the high temperatures at which the converters must operate. Thus it is useful to determine the relative fatigue resistance of two commercially available mat materials of high refractoriness and good resilience under vibration stress at high temperatures.

The two materials to be evaluated in this test are refractory Mat A, a mullite-based fibrous non-intumescent mat material, and refractory Mat B, a coarser mullite-based fibrous non-intumescent mat. Catalytic converters are assembled employing each of these mat materials to support ceramic catalyst support honeycombs within welded steel converter enclosures. The thicknesses of the support layers and diameters of the enclosures are adjusted in each case to obtain approximately equivalent compressive retaining forces on the honeycombs disposed in the converter enclosures.

Data concerning converter operating conditions for the motorcycle environment in which these converters will be used is collected by equipping a motorcycle converter with accelerometers and exposing the vehicle to a range of reasonable driving conditions. The results indicate that the most severe motion of the substrate (approximately 2000 microinches of vibration amplitude) occurs during a resonance condition arising at a converter vibration frequency of 2000 Hz. This amplitude is very likely above the high-temperature endurance limit for either of the two candidate honeycomb mounting systems being considered. Therefore vibration testing under approximate use conditions will be useful in predicting the expected service life for each of these systems.

A number of identically prepared converters incorporating Mat A as the support material for the ceramic honeycomb are first subjected to room-temperature testing. Each test converter is mounted in apparatus substantially as shown in FIG. 1, and vibration is initiated at a frequency of 150 Hz and a pre-selected converter displacement amplitude in the range of about 1500–8000 microinches. In each case, vibration is continued until the peak force detected at the load cell drops to 50% of its value at the start of the test, and the number of vibration cycles at this arbitrary force level is recorded.

After the room-temperature tests have been completed, additional high-temperature vibration tests at the same vibration frequency are conducted at two of the pre-selected converter vibration amplitudes used for the room temperature tests. During the high-temperature tests, the internal converter heater and the external converter enclosure are activated in order to maintain an internal converter temperature of about 1000° C. and an external converter enclosure temperature of about 800° C. throughout. Again, the number of vibration cycles needed to reduce the load cell forces to 50% of their initial value is recorded.

Figure 2:
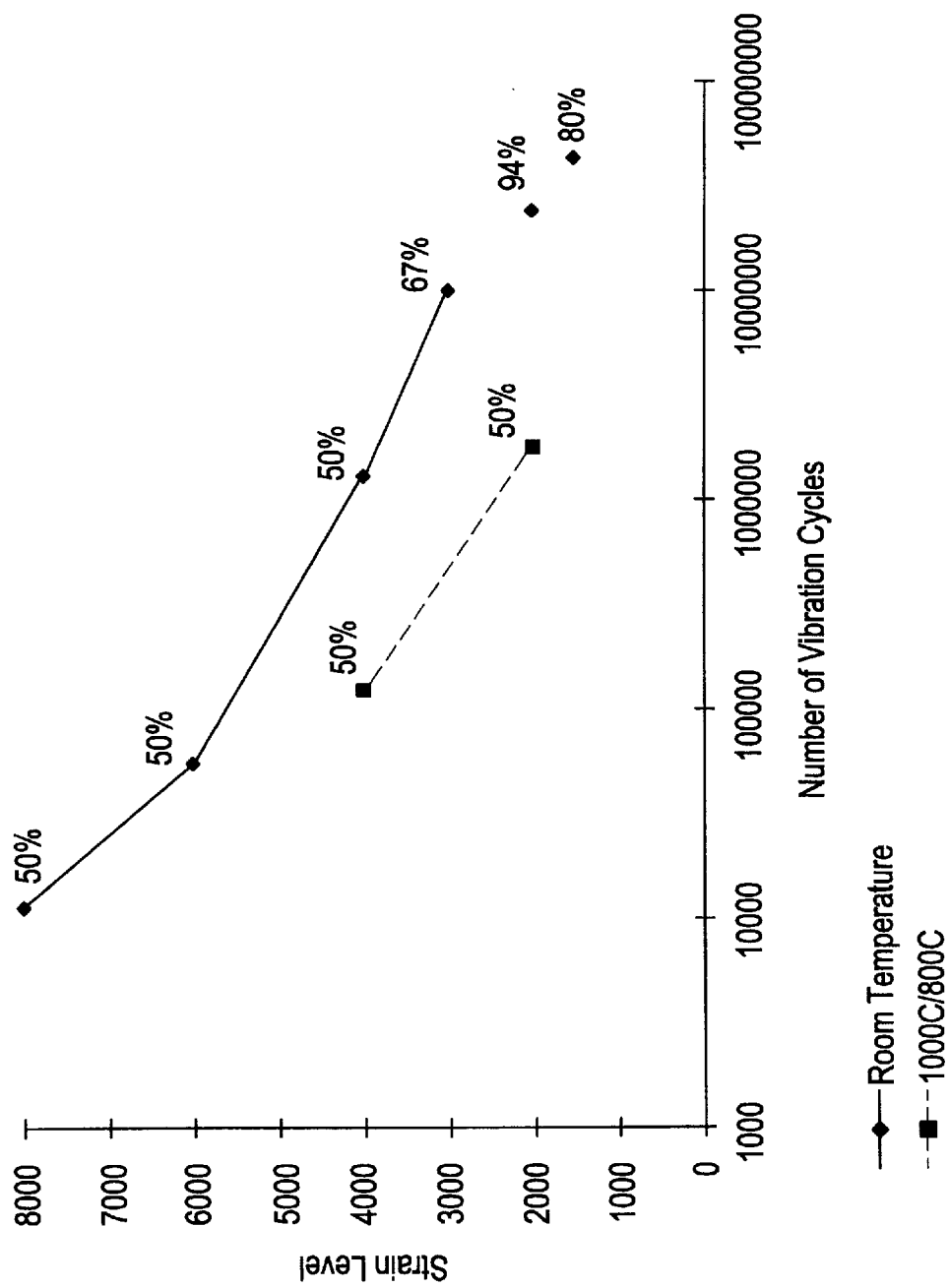

Results for such a series of tests are reported in FIG. 2 of the drawing, which is a plot of the 50% "failure" points, and selected higher performance points, for each of the tests conducted. The plotted points are labeled with the fraction of the initial load cell force remaining at the termination of the test. For each of the performance points plotted, the pre-selected vibration amplitude or strain level applied to the converter enclosure is shown in microinches on the vertical axis and the number of vibration cycles to reach the indicated performance level is shown on the horizontal axis.

A study of the data in FIG. 2 indicates that the room temperature endurance level for converters employing Mat A as a honeycomb support is a vibration amplitude of approximately 3000 microinches. That is, extending the testing beyond 107 vibration cycles at the 3000 microinch vibration amplitude could eventually have caused load cell force to drop to 50%, but similar test extensions at 2000 microinches and 1500 microinches would probably not. This latter conclusion is supported by the fact that only partial and inconsistent reductions in load cell force were observed after tens of millions of vibration cycles at these lower vibration amplitudes.

Considering next the high-temperature test results, 50% "failure" reductions in load cell force are observed in the converters tested at 1000° C. after cycle counts in the range of only a few hundred thousand to a few million cycles. The trend of this data suggests that the endurance limit of the Mat A honeycomb mounting would probably be below about 1000 microinches at these vibration frequencies for converter operation at 1000° C.

Preliminary vibration test results obtained from evaluations of catalytic converters incorporating Mat B as the resilient honeycomb mounting material show a significant performance advantage over the Mat A samples. In room temperature testing at identical vibration frequencies, and at vibration amplitudes Up to and including 8000 microinches, no significant reduction in initial load cell force is observed in converter samples incorporating the Mat B material over testing intervals up to about 70 million cycles.

More significantly, high temperature converter testing under the same conditions as described above for the Mat A mounting material show a substantial performance advantage for the Mat B mounting. Converters incorporating the Mat B mounting material and internally heated to 1000° C. during testing at vibration amplitudes of 4000 and 8000 microinches retain 50% of the initial load cell force through vibration intervals in excess of 14 million cycles and 15 million cycles, respectively.

It will be appreciated that results can provide a quantitative comparison of the projected service lives of resilient honeycomb catalyst support materials under high temperature use conditions. In this case, for example, the high temperature data suggest that the Mat B material should demonstrate a service life as much as 15 times the expected service life of the Mat A material, under equivalent use conditions.

Although most effective to provide relative performance measurements, the data produced by vibration testing in accordance with the method of the invention may also be used to estimate absolute service life in some cases. For example, if it is assumed that a loss of 50% of the initial load cell force corresponds to an expected failure condition in a typical converter mounting, then a converter incorporating a mounting of the Mat A material should withstand approximately 1.77 million converter vibration cycles of 2000 microinch amplitude at a 1000° C. honeycomb support temperature and 800° C. converter enclosure temperature.

In the actual use environment, this most damaging vibration condition is not constant but occurs only when the exhaust system is fully heated, and then only within intermittent intervals of converter resonance, each interval lasting perhaps I second (i.e. 2000 cycles). If it is projected that vehicle will be driven daily and that the resonance condition only occurs for a total of two seconds/day while at peak exhaust system temperatures, then the anticipated 1.77 million vibration cycle life of the converter would extend for a vehicle use period in excess of two years.

It will be apparent from the foregoing that the method and apparatus of the invention offer a means to quantify the durability differences between various canning processes as well as to assess mat durability. The effects of various canning parameters, the variability of canning systems, changes in converter performance from lot to lot, and many other converter performance characteristics can be quantitatively determined. Unusual use conditions can also be simulated, since the honeycomb catalyst support can be heated to any desired temperature profile, and heated without the use of expensive combustion engine sources of hot exhaust gas.

The simulation flexibility of the testing method of the invention greatly enhances its utility as an accelerated testing tool, capable of applying thermal and vibration forces even more severe than those experienced on a motor vehicle. This approach generates endurance limit curves of much greater predictive value than the pass/fail result of conventional engine tests and the cost of generating this information is substantially reduced. The opportunity thus presented to model converter performance and design will permit lower converter manufacturing costs, since the over-engineering required to insure service life in the absence of an adequate converter life predictor may now be avoided.

We claim:

1. Apparatus for the vibration testing of a catalytic converter comprising:

a support structure for rigidly supporting a catalytic converter to be tested;

a vibrator connected to the support structure for vibrating the support structure and the catalytic converter under predetermined vibration conditions;

a heater for preferentially heating a catalyst support honeycomb mounted within the converter; and a sensor for attachment to the honeycomb, the sensor being adapted to sense force or acceleration applied to the honeycomb in the course of testing.

2. Apparatus in accordance with claim 1 wherein support structure is a load frame.

3. Apparatus in accordance with claim 2 wherein the load frame is attached to an electrodynamic shaker table.

4. Apparatus in accordance with claim 3 wherein the electrodynamic shaker table includes means for controlling the frequency of table vibration.

5. Apparatus in accordance with claim 4 wherein the electrodynamic shaker table includes means for controlling the amplitude of table vibration.

6. Apparatus in accordance with claim 1 wherein the heater is an electrical heating element.

7. Apparatus in accordance with claim 6 wherein the electrical heating element is disposed at least partly within an interior of the catalyst support honeycomb.

8. Apparatus in accordance with claim 7 wherein the catalyst support honeycomb comprises open cells, and wherein the electrical heating element is disposed at least partially within selected ones of the open cells.

9. Apparatus in accordance with claim 1 wherein the sensor is adapted to sense at least one of the acceleration or force applied to the catalyst support honeycomb.

10. Apparatus in accordance with claim 2 wherein the sensor comprises a load cell mounted on the load frame and mechanically attached to the honeycomb by means of a connector for transmitting honeycomb vibrations to the load cell.

11. Apparatus in accordance with claim 1 which further comprises an external heater for heating an exterior shell of the converter.

12. A method for testing the durability of a catalytic converter incorporating a catalyst support honeycomb supported by a resilient mounting material within an exterior converter enclosure which comprises the steps of simultaneously:

vibrating the exterior converter enclosure; while heating the catalyst support honeycomb to at least one predetermined testing temperature; and while detecting at least one of an force or an acceleration applied to the catalyst support honeycomb by the vibrating exterior enclosure and resilient mounting material.

13. A method in accordance with claim 12 wherein the exterior converter enclosure is vibrated at one or a plurality of controlled vibration frequencies.

14. A method in accordance with claim 12 wherein the exterior converter enclosure is vibrated at one or a plurality of controlled vibration amplitudes.

15. A method in accordance with claim 12 wherein vibration of the exterior converter enclosure is accomplished by rigidly attaching the enclosure to a rigid support member adapted for vibration at a controlled predetermined vibration amplitude and a controlled predetermined vibration frequency.

16. A method in accordance with claim 12 wherein the applied force or acceleration is detected by sensing means rigidly attached to the catalyst support honeycomb.

17. A method in accordance with claim 16 wherein the applied force is determined by means of a load cell mechanically connected to the catalyst support honeycomb.

18. A method in accordance with claim 12 wherein the catalyst support honeycomb is electrically heated.

19. A method in accordance with claim 18 wherein the catalyst support honeycomb is heated by means of an internal electrical heating element.

20. A method in accordance with claim 12 which comprises the additional step of simultaneously heating the external converter enclosure.

* * * * *